(12) United States Patent
Liu et al.

(10) Patent No.: US 9,045,543 B2
(45) Date of Patent: Jun. 2, 2015

(54) HUMANIZED ANTI-CD20 MONOCLONAL ANTIBODY

(75) Inventors: Jie Liu, Shandong (CN); Yongke Zhang, Shandong (CN)

(73) Assignee: Bioex Therapeutics, Inc., Pudong, Shanghai (CN)

( * ) Notice: Subject to any disclaimer, the term of this patent is extended or adjusted under 35 U.S.C. 154(b) by 0 days.

(21) Appl. No.: 13/634,072

(22) PCT Filed: Mar. 16, 2011

(86) PCT No.: PCT/CN2011/000423
§ 371 (c)(1),
(2), (4) Date: Sep. 11, 2012

(87) PCT Pub. No.: WO2011/113308
PCT Pub. Date: Sep. 22, 2011

(65) Prior Publication Data
US 2013/0089540 A1    Apr. 11, 2013

(30) Foreign Application Priority Data
Mar. 17, 2010    (CN) .......................... 2010 1 0150303

(51) Int. Cl.
*C07K 16/28* (2006.01)
*C07K 16/30* (2006.01)
*A61K 39/395* (2006.01)
*A61K 39/00* (2006.01)

(52) U.S. Cl.
CPC ......... *C07K 16/2887* (2013.01); *C07K 2317/56* (2013.01); *A61K 2039/505* (2013.01); *C07K 2317/24* (2013.01); *C07K 2317/732* (2013.01); *C07K 2317/734* (2013.01)

(58) Field of Classification Search
CPC ....................... C07K 16/2887; C07K 2317/94
See application file for complete search history.

(56) References Cited

U.S. PATENT DOCUMENTS

| 2003/0219433 A1 | 11/2003 | Hansen et al. |
| 2003/0219633 A1 | 11/2003 | Sulin et al. |
| 2008/0089885 A1 | 4/2008 | Smith et al. |
| 2011/0263825 A1 | 10/2011 | Uchiyama et al. |

OTHER PUBLICATIONS

Zhang et al., "Characterization of a Novel Humanized Anti-CD20 Antibody with Potent Anti-Tumor Activity against Non-Hodgkin's Lymphoma", Cell Physiol Biochem 2013;32:645-654.*

Nielsen et al., "Quantitative Predictions of Peptide Binding to Any HLADR Molecule of Known Sequence: NetMHCIIpan", PLoS Comput Biol 4(7): 1-10, 2008.*
Cragg, Mark S., et al.; "The Biology of CD20 and Its Potential as a Target for mAb Therapy"; Curr Dir Autoimmum. Basel, Karger, 2005, vol. 8; pp. 140-174.
Reff, Mitchell E., et al.; "Future of Monoclonal Antibodies in the Treatment of Hematologic Malignancies"; Cancer Control Mar./Apr. 2002, vol. 9, No. 2; 15 pgs.
Clynes, Raphael A., et al.; "Inhibitory Fc receptors modulate in vivo cytoxicity against tumor targets"; Nature Medicine, vol. 6, No. 4, Apr. 2000; 4 pgs.
Pedersen, Irene M., et al.; "The chimeric anit-CD20 antibody rituximab induces apoptosis in B-cell chronic lymphocytic leukemia cells through a p38 mitogen activated protein-kinase-dependent mechanism"; Blood 2002:99; pp. 1314-1319.
Gopal, Ajay K., et al.; Clinical applications of anti-CD20 antibodies; J Lab Clin Med 1999:134 pp. 445-450.
Cheson, Bruce D.; "Monoclonal antibody therapy of chronic lymphocytic leukemia"; Cancer Immunol Immunother (2006) 55: pp. 188-196.
Du, J. et al., "Structural basis for recognition of CD20 by therapeutic antibody Rituximab"; J. Biol.Chem., May 18, 2007, vol. 282, No. 20, pp. 15073-15080.
Summers, Kelly M., et al.; "Rituximab Treatment of Refractory Rheumatoid Arthritis"; The Annals of Pharmacotherapy; Dec. 2005, vol. 39; p. 2091; 5 pgs.
Cartron, Guillaume, et al.; "Pharmacokinetics of rituximab and its clinical use: Thought for the best use?"; Critical Reviews in Oncology/Hematology 62 (2007) pp. 43-52.
Riechmann, Lutz, et al.; "Reshaping human antibodies for therapy"; Nature vol. 332, p. 323; Mar. 24, 1988; 5 pages.
Reff, Mitchell E., et al.; "Depletion of B Cells In Vivo by a Chimeric Mouse Human Monoclonal Anitbody to CD20"; Blood, vol. 83, No. 2, Jan. 15, 1994; pp. 435-445.

* cited by examiner

*Primary Examiner* — Ronald Schwadron
(74) *Attorney, Agent, or Firm* — Blank Rome LLP

(57) ABSTRACT

The present invention discloses a humanized anti-CD20 antibody, which comprises a heavy chain comprising a polypeptide according to one of SEQ ID NO: 15, SEQ ID NO: 16, or SEQ ID NO: 36; and a light chain comprising a polypeptide according to one of SEQ ID NO: 34, SEQ ID NO: 35, or SEQ ID NO: 37. Comparing to murine-derived antibodies and human-mouse chimeric antibodies, said humanized anti-CD20 antibody maintains or improves high binding activity of the variable regions, meanwhile reduces the immunogenicity of chimeric antibodies, consequently achieves the effect of reducing medicine side effects and improving clinical treatment. The antibody disclosed by the present invention is efficiently expressed in animal cells, can be used for industrial production. It could be used in treating B cell lymphoma, leukaemia, or B cell-associated autoimmune disease with a wide application prospect.

6 Claims, 8 Drawing Sheets

Figure 1

```
                        <---------------FR1--------------->
         2B8 HC         QVQLQQPGAELVKPGASVKMSCKASGYTFT
    IGHV7-4-1*03        ....V.S.S..K.......V..........
    IGHV7-4-1*02        ....V.S.S..K.......V..........
      IGHV1-8*01        ....V.S...VK.......V..........
      IGHV1-3*01        ....V.S...VK.......V..........
      IGHV1-2*04        ....V.S...VK.......V..........
     IGHV1-46*03        ....V.S...VK.......V..........
      IGHV1-2*02        ....V.S...VK.......V..........
      IGHV1-2*01        ....V.S...VK.......V..........
    IGHV7-4-1*01        ....V.S.S..K.......V..........
     IGHV1-46*01        ....V.S...VK.......V..........
```

Figure 2

```
                        <------FR2--->
         2B8 HC         WVKQTPGRGLEWIG
     IGHV4-55*09        ..R.P..K......
     IGHV4-55*08        ..R.P..K......
     IGHV4-55*06        ..R.P..K......
     IGHV4-55*02        ..R.P..K......
     IGHV3-72*02        ..R.A..K....V.
     IGHV3-72*01        ..R.A..K....V.
     IGHV4-55*01        ..R.P..K......
     IGHV3-71*01        ..R.A..K....V.
     IGHV3-49*04        ..R.A..K....V.
     IGHV4-55*05        ..R.P..K......
```

Figure 3

```
                    <-------------FR3------------->
      2B8 HC        KATLTADKSSSTAYMQLSSLTSEDSAVYYCAR
   IGHV1-69*10      RV.I.....T.....E....R...T.......
   IGHV1-69*09      RV.I.....T.....E....R...T.......
   IGHV1-69*06      RV.I.....T.....E....R...T.......
   IGHV1-69*04      RV.I.....T.....E....R...T.......
   IGHV1-69*08      RV.I.....T.....E....R...T.......
   IGHV1-69*02      RV.I.....T.....E....R...T.......
   IGHV1-69*12      RV.I...E.T.....E....R...T.......
   IGHV1-69*11      RV.I...E.T.....E....R...T.......
   IGHV1-69*01      RV.I...E.T.....E....R...T.......
   IGHV1-69*13      RV.I...E.T.....E....R...T.......
```

Figure 4

```
            <---FR4--->
   2B8HC    WGAGTTVTVSA
    JH1     WGQGTLVTVSS
    JH4     WGQGTLVTVSS
    JH5     WGQGTLVTVSS
    JH2     WGRGTLVTVSS
    JH3     WGQGTMVTVSS
    JH6     WGQGTTVTVSS
```

Figure 5

```
                <---------FR1-------->
      2B8 LC    QIVLSQSPAILSASPGEKVTMTC
   IGKV6D-41*01 DV.MT....F..VT.......I..
   IGKV3D-20*01 E...T....T..L....RA.LS.
   IGKV3-NL5*01 E...T....T..L....RA.LS.
   IGKV3-20*02  E...T....T..L....RA.LS.
   IGKV3-11*02  E...T....T..L....RA.LS.
   IGKV3-NL4*01 E...T....T..L....RA.LS.
   IGKV3-11*01  E...T....T..L....RA.LS.
   IGKV3D-11*01 E...T....T..L....RA.LS.
   IGKV3-NL2*01 E...T....T..L....RA.LS.
   IGKV3-NL1*01 E...T....T..L....RA.LS.
```

Figure 6

```
                <-------FR2---->
      2B8 LC    WFQQKPGSSPKPWIY
   IGKV1-16*02  .......KA..SL..
   IGKV1-16*01  .......KA..SL..
   IGLV2-5*02   .Y..H..TV...M..
   IGLV2-5*01   .Y..H..TV...M..
   IGLV7-43*01  .......QA.RAL..
   IGLV7-46*02  .......QA.RTL..
   IGLV7-46*01  .......QA.RTL..
```

Figure 7

```
                        <--------------FR3------------>
         2B8 LC         GVPVRFSGSGSGTSYSLTISRVEAEDAATYYC
     IGKV6D-21*01       ...S.........DFT...NSL..........
      IGKV6-21*01       ...S.........DFT...NSL..........
     IGKV6D-41*01       ...S.........DFTF...SL..........
      IGKV3-20*02       .I.A.........DFT.....L.P..F.V...
     IGKV3-NL3*01       .I.A.........EFT.....LQS..F.V...
     IGKV1D-43*01       ...S.........D.T.....SLQP..F....
     IGKV1-NL1*01       ...S.........D.T.....SLQP..F....
```

Figure 8

```
                <--FR4--->
       2B8 LC   FGGGTKLEIK
          JK1   FGQGTKVEIK
          JK2   FGQGTKLEIK
          JK3   FGPGTKVDIK
          JK4   FGGGTKVEIK
          JK5   FGQGTRLEIK
```

Figure 9

9A  QVQLVQSGAEVKKPGASVKVSCKASGYTFTSYNMHWVRQPPGKGLEWIGAIYPGNGDTSYNQKFKG
    RVTITADESTSTAYMELSSLRSEDTAVYYCARSTYYGGDWYFNVWGQGTTVTVSS

9B  QVQLVQSGAEVKKPGASVKVSCKASGYTFTSYNMHWVRQAPGKGLEWIGAIYPGNGDTSYNQKFKG
    RVTITADKSTSTAYMELSSLRSEDTAVYYCARSTYYGGDWYFNVWGQGTTVTVSS

9C  DVVMTQSPAFLSVTPGERVTITCRASSSVSYIHWFQQKPGKAPKSLIYATSNLAS
    GVPSRFSGSGSGTDFTLTINSLEAEDAATYYCQQWTSNPPTFGGGTKVEIK

9D  DVVMTQSPAFLSVTPGEKVTITCRASSSVSYIHWFQQKEGKAPKPLIYATSNLAS
    GVPSRFSGSGSGTDFTLTINSLEAEDAATYYCQQWTSNPPTFGGGTKVEIK

Figure 10

Humanized VH

```
                  <--------FR1-------------------->CDR1 <---FR2------>
hVH-1 (Seq ID NO:16)  QVQLVQSGAEVKKPGASVKVSCKASGYTFTSYNMHWVRQAPGKGLEWIG
hVH-2 (Seq ID NO:38)  QVQLVQSGAEVKKPGASVKVSCKASGYTFTSYTMHWVRQAPGKGLEWIG

CDR2            <--------------FR3-------------->
hVH-1 (Seq ID NO:16)  AIYPGNGDTSYNQKFKGRVTITADKSTSTAYMELSSLRSEDTAVYYCAR
hVH-2 (Seq ID NO:38)  AIYPGNSDTNYNQKFKGRVTITADKSTSTAYMELSSLRSEDTAVYYCAR

CDR3      <---FR4--->
hVH-1 (Seq ID NO:16)  STYYGGDWYFNVWGQGTTVTVSS
hVH-2 (Seq ID NO:38)  STYYGGDWHFEVWGQGTTVTVSS
```

Figure 11

Humanized VK

```
                <--------FR1---------->    CDR1    <----FR2------>
hVK-1 (Seq ID NO:35)  DVVMTQSPAFLSVTPGEKVTITCRASSSVSYIHWFQQKPGKAPKPLIY
hVK-2 (Seq ID NO:37)  DVVMTQSPAFLSVTPGEKVTITCRASSSVSYIHWFQQKPGKAPKPLIY

CDR2     <---------------FR3--------------->
hVK-1 (Seq ID NO:35)  ATSNLASGVPSRFSGSGSGTDFTLTINSLEAEDAATYYC
hVK-2 (Seq ID NO:37)  ATSNLASGVPSRFSGSGSGTDFTLTINSLEAEDAATYYC

CDR3    <--FR4--->
hVK-1 (Seq ID NO:35)  QQWTSNPPTFGGGTKVEIK
hVK-2 (Seq ID NO:37)  QQWTSKPPTFGGGTKVEIK
```

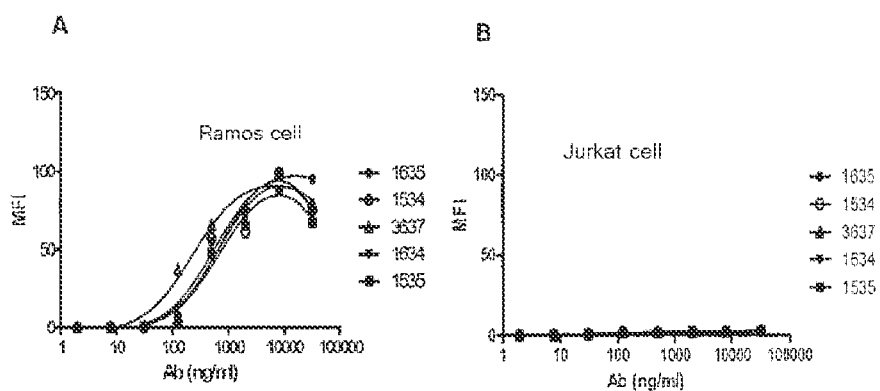

Figure 12

HUMANIZED ANTI-CD20 MONOCLONAL ANTIBODY

FIELD OF THE INVENTION

The present invention generally relates to the biomedical field, particularly to the techniques of humanized monoclonal antibodies, recombinant DNA as well as the expression of antibodies. Compared with murine antibodies, chimeric antibodies and other humanized antibodies, the humanized anti-CD20 antibody according to the present invention further reduces the immunogenicity while maintains outstanding activity of antigen recognition and in vivo and/or in vitro anti-tumor activity, thus provides better clinical application.

BACKGROUND OF THE INVENTION

CD20 molecule, with a molecule weight of about 35 kDa, is one of members of MS4A protein family which has four transmembrane domains and contains both their C and N ends within the cell (Cragg, et al, Curr. Dir. Autoimmun, 8: 140-174), CD20, as a membrane protein which expresses on the surface of B lymphocytes, closely relates to $Ca^{2+}$-conductance in B lymphocytes and regulates the differentiation and proliferation of B lymphocytes. CD20 is exclusively expressed on pre-B lymphocytes, premature B lymphocytes, mature B lymphocytes and activated B lymphocytes, but absent in plasma cells, lymphoid pluripotent stem cell cells and other tissues. The natural ligand of CD20 is still unknown. Because CD20 is highly expressed by more than 90% B-cell Non-Hodgkin's lymphoma, CD20 is an ideal target for antibody therapy of B-cell lymphoma (Blood 63 (6): 1424-1433, 1984). The anti-CD20 monoclonal antibody (mAb) has been proved to have an outstanding in vivo and in vitro effect on B-cell lymphoma (Reff M E et al, Cancer Control 2002; 9:152-66). Upon binding to CD20, anti-CD20 antibody may kill tumor cells through ADCC (Clynes R A et al. Nat Med, 2000; 6:443-6), through. CDC (Harjunpaa A, et al, Scand J Immunol 2000; 51:634-41), and/or direct induction of apoptosis of tumor cell (Apoptosis; Pedersen I M, et al, Blood 2002; 99:1314-9). Because anti-CD20 antibody only kills B cells carrying CD20 surface antigen, it greatly reduces the side effect compared with chemotherapy, thus provides an effective and safe targeting therapy for NHL patients. In recent years, basic research and clinic application of anti-CD20 antibody has been widely investigated. Rituximab, ZEVALIN® (ibritumomab tiuxetan) and BEXXAR® (tositurnornab and iodine I131) have been approved by FDA for treatment of NHL in 1997, 2002 and 2003, respectively. Rituximab is a human-mouse chimeric monoclonal antibody containing variable region derived from murine monoclonal antibody and constant region from human IgG1 heavy and K light chain (Gopal and Press, J Lab Clin Med, 1999; 134:445-450). ZEVALIN® (ibritumomab tiuxetan)is a murine monoclonal antibody conjugated with radionuclide $^{90}Y$. BEXXAR® (tositumomab and iodine I131)is murine monoclonal antibody conjugated with radionuclide $^{131}I$. Treatment of refectory NHL with rituximab only achieved a response rate of around 50%; when combined with chemotherapy drug, the response rate can reach up to 90-100%. Because CD20 is also expressed in hairy cell leukemia and B-cell chronic lymphocytic leukemia, more and more indications for anti-CD20 therapy have been applied recently. Rituximab, in combination with chemotherapy, has provided satisfying effect on chronic lymphocytic leukemia (Cheson, et al. 2006, Cancer Immunol. Immunother. 55: 188-196). Due to its efficient therapeutic effect and less side effects, rituximab became one of the bestselling anti-cancer drugs with close to 5 billion sales in 2008.

In addition, B cells also play a central role in pathogenesis of autoimmune disease. Many autoimmune diseases are associated with abnormal activation of B-cell, production of autoantibody and mediation of autoimmune response. Examples include acute idiopathic thrombocytopenic purpura and chronic idiopathic thrombocytopenic purpura, myasthenia gravis, lupus nephritis, lupus erythematosus and rheumatoid arthritis. The most common treatments are corticosteroids and cytotoxic drugs, which can be very toxic. These drugs have adverse effects on the bone marrow, liver and kidney, also suppress the entire immune system and result in serious infection. Therapies directed against B cell have been proved to be effective on the treatment of human autoimmune disease, Rituximab is effective on decreasing B lymphocytes in vivo. Such treatment can eliminate auto-antibodies produced by B cells. Rituximab is furthermore found use in autoimmune diseases, such as rheumatoid arthritis, wherein it has been shown to markedly improve symptoms. Rituximab has been approved by FDA for patients suffered from moderate to advanced rheumatoid arthritis (Summers et al, 2005. Ann. Pharmacother. 39: 2091-2095).

However, the biggest problem of administrating therapeutic antibody is the immune response resulting from the human response to foreign antibody protein, namely anti-antibody reaction (AAR). The murine antibody; working as foreign protein, can stimulate the human body repeatedly and lead to hyper allergic reaction, namely human anti-mouse antibody reaction (HAMA). This leads to the neutralization of murine antibody by anti-antibody, fast clearance of murine antibody or even leads to death caused by severe allergic reaction. In addition, due to the lack of effector function of human antibody (such as ADCC and CDC effect), the therapeutic effect of murine antibody is compromised. Although rituximab is human-mouse chimeric antibody comprising human Fc fragment, it still contains murine antibody sequence in the variable region of both heavy chain and light chain. The murine derived sequence was considered foreign to human system and causes immunogenicity that leads to production of neutralizing antibody and reduces drug efficacy when administered constantly. Especially in the cases of long period treatment with a lower dose, it is more likely to have immunogenicity. Higher immunogenicity of rituximab was exhibited in its treatment of autoimmune disease (such as SLE) than that of NHL (Cantron G. et al, Critical Reviews in Oncology/Hematology, Volume 62).

In order to further decrease the immunogenicity, "CDR graft" became major procedure of humanization of antibody (Riechman et al. Nature, 332:323-327, 1988). Such technique reduces the immunogenicity caused by mouse frame sequence through grafting mouse CDR regions onto framework of human antibody. Currently, this technique has created humanized anti-CD20 antibody 2H7 (Genentech, CN 101418045A), A20 mAb (Immunomedics, Inc., CN 1662557A) and H1286/1373 (VACCINEX), 1K1791 mAb (Osaka University, WO 2009031230 A1) as well as 9D3 mAb (CP Guojian Pharmaceutical Co., Ltd).

Even though the combination of amino acids of these humanized framework and murine CDR still can be recognized by T cells and cause immune response. The recognition of foreign protein by T cell is mainly due to the presentation to T cell receptor by MHC-II expressed on APC surface which binds to protein polypeptide. This further leads to activation of lymphocyte and immune reaction. Therefore, when designing and choosing the humanized framework, the peptide sequence from the framework should have minimum binding with MHC II molecules (HLA-DR), thus minimizes immune response caused by humanized antibody. The humanized antibody of the present invention is based on the sequence of murine 2B8 (Reff, M, E. et al (1994) Blood 83:435-445) and the humanization method described in this application. Through design and selection of the human germline framework sequence that has minimal binding sites with MHC II (HLA-DR), humanized 2B8 molecules were created with much lower immunogenicity. Moreover, using method of molecular docking, CDR sequence can be further modified to maintain or improve antigen recognition and in vivo and/or in vitro anti-tumor activity. These humanized anti-CD20 antibodies also have widely application in the treatment of abnormal activation of B cell and autoimmune diseases.

BRIEF SUMMARY OF THE INVENTION

The present invention relates to a humanized anti-CD20 antibody, the heavy chain variable region of the antibody consists of the amino acids sequence of SEQ ID NO:15, SEQ ID NO:16 or SEQ ID NO:36; and the light chain variable region consists of amino acids sequence of SEQ ID NO:34, SEQ ID NO:35 or SEQ ID NO: 37.

The present invention relates to a humanized anti-CD20 antibody, which is the antibody as shown in Table 1, that is humanized antibody 1534, 1634, 1535, 1635 or 3637.

The antibodies described above, the antibody may be a monovalent antibody, multivalent antibody, single chain antibody, antibody having single antigen binding arm, or antibody having Fc region modified for the purpose of toxic agent conjugation.

The present invention relates to a DNA molecular that encodes the antibody described above.

The present invention relates to a RNA molecule that encodes the said antibody, or contains the complementary sequence of DNA sequence that encodes the antibody described above.

The present invention relates to an expression vector that comprises DNA molecular encoding the antibody described above.

The present invention relates to a host cell that comprises vector, said vector contains DNA molecular encoding the antibody described above.

The present invention relates to a composition comprising the antibody described above and a pharmaceutically acceptable carrier.

The present invention relates to a composition that contains the antibody described above and preparation formulated from pharmaceutically acceptable excipient, said composition is used for clinical treatment of B cell lymphoma, leukemia and various autoimmune diseases associated with B cell.

The present invention relates to a product that contains a container and composition within the container, said composition comprises the antibody described above.

The present invention relates to the use of humanized CD20-binding antibody as described above in the preparation of drugs for the treatment of CD20 positive malignancy, B cell lymphoma, B cell CLL, autoimmune diseases, such as acute idiopathic thrombocytopenic purpura, chronic idiopathic thrombocytopenic purpura, myasthenia gravis, lupus nephritis, lupus erythematosus and rheumatoid arthritis.

The present invention relates to a method for screening and preparing the humanized antibody as described above: analyzing the sequence of variable region of heavy chain of murine anti-CD20 antibody 2B8; aligning sequence of FR1, FR2, FR3 and FR4 of variable region of heavy chain with sequence database of human antibody genes; identifying corresponding sequences of human germline antibody variable region (which has much lower immunogenicity than mature antibody) which are similar to the sequences of FR1, FR2, FR3 and FR4 of heavy chain variable region of murine antibody 2B8; then analyzing the binding affinity of said sequence with HLA-DR molecule by in-silicon analysis (such as using NetMHCIIpan software or self-designed software); selecting the framework sequence with the lowest affinity; and as such finally determining the humanized sequence of FR1, FR2, FR3 and FR4 of heavy chain variable region. Based on the structure of such framework, an in-silicon molecular modeling is used to analyze the stereo structure of variable region of murine 2B8 anti-CD20 antibody; and then the corresponding framework amino acid residues of murine 2B8 necessary for the maintenance of CDR configuration are determined (linear positions adjacent to CDR antigen binding site or amino acid residues located within 6 Å away from CDR); various combinations of sequences of humanized heavy chain variable region (preferably said sequence) are designed. Similarly, analyzing the sequence of variable region of light chain of murine anti-CD20 antibody 2B8; aligning sequence of FR1, FR2, FR3 and FR4 of variable region of light chain with sequence database of human antibody genes (NCBI Ig BLAST); identifying corresponding sequences of human germline antibody variable region which are similar to the sequences of FR1, FR2, FR3 and FR4 of light chain variable region of murine antibody 2B8; then analyzing the binding affinity of said sequence with HLA-DR molecule by using in-silicon analysis; selecting the framework sequence with the lowest affinity; and as such finally, determining the humanized sequence of FR1, FR2, FR3 and FR4 of light chain variable region. Based on the structure of such framework, an in-silicon molecular modeling is used to analyze the stereo structure of variable region of murine 2B8 anti-CD20 antibody; and then the corresponding framework amino acid residues of murine 2B8 necessary for the maintenance of CDR configuration are determined; various combinations of sequences of humanized light chain variable region are designed.

On such a basis, molecular docking method can be used to analyze the stereo binding of the epitope of CD20 ($^{170}$ANPS$^{173}$) and its surrounding amino acid residues $^{168}$E, $^{169}$P, $^{174}$E and $^{175}$K to humanized heavy chain variable region. By calculating static electricity, salvation, Van der Waals force and entropy, the amino acids in sequence of CDR1, CDR2 and CDR3 can be optimized to improve the binding of CDR region to CD20 antigenic epitope, and thus obtain antibody with better activity. Preferably, the heavy chain variable region has SEQ ID NO: 36;

The variable region of HC and LC obtained as above are connected to constant region of HC and LC, preferably constant region of HC of IgG1 and constant region of LC derived from healthy human B lymphocyte. Thus the obtained full length HC and LC are different from those antibody molecules generated by corribination of HC and LC.

The present invention provides a novel humanized anti-CD20 antibody characterized by the further decreased immunogenicity of humanized antibody. The antibody consists of the HC variable region amino acid sequence that is identical to SEQ ID No.15 or SEQ ID No.16 and LC variable region amino acid sequence that is identical to SEQ ID No.34 or SEQ ID No.35. The antibody according to the invention can also generated by CDR optimization at the position shown in FIG. 10 and at the position shown in FIG. 11 in order to maintain and enhance its biological activity. The humanized anti-CD20 antibodies generated by various combinations of HC and LC are shown in Table 1.

The antibody according to the present invention can be a monovalent antibody, a multivalent antibody or a single chain antibody. The present invention relates to a method of inhibiting CD20 positive B lymphocyte by using such antibody, as well as the use thereof in the field of medicine.

Fc fragment of the antibody according to the present invention can also be modified to improve the function of effector. For example, the substitution or glycosylation of one or more amino acids in Fc region may enhance the function of effector and thus enhance antibody dependent cell-mediated cytotoxicity (ADCC) and/or complement dependent cytotoxicity (CDC).

Fc fragment of the antibody according to the present invention can also be conjugated with radioisotope, chemotherapy drug or toxin, and thus enhances antibody cytotoxicity.

In order to achieve the Objectives as above, the present invention comprises the following technical solutions:

1. Design and Preparation of Humanized Anti-CD20 Antibody

The sequence of murine anti-CD20 2B8 VH was analyzed, and VH FR1, FR2, FR3 and FR4 were compared with sequence database of human antibody gene (NCBI Ig BLAST), so as to identify corresponding sequences of human germline antibody variable region (which has much lower immunogenicity than mature antibody) which are similar to the sequences of FR1, FR2, FR3 and FR4 of heavy chain variable region of murine antibody 2B8. And then the binding affinity of said sequence with HLA-DR molecules (DRB1*0101, DRB1*1501, DRB1*0301, DRB1*0401, DRB1*0404, DRB1*0405, DRB1*0701, DRB1*0802, DRB1*0901, DRB1*1101, DRB1*1302, DRB3*0101, DRB4*0101, DRB5*0101, DQB1*0301 and DQB1*0302, those molecules as shown above have represented most HLA-II molecules in the world) was analyzed by in-silicon analysis. The framework sequences with lowest affinity were identified, and finally, the humanized sequences of FR1, FR2, FR3 and FR4 of heavy chain variable region were respectively determined as FR1: SEQ ID No. 3, FR2: SEQ ID No. 5/SEQ ID No. 6, FR3: SEQ ID No.8 and SEQ ID No. 9, FR4: SEQ ID No. 14. Based on the structure of such framework, an in-silicon molecular modeling was used to analyze the stereo structure of variable region of murine 2B8 anti-CD20 antibody; and then the corresponding framework amino acid residues of murine 2B8 necessary for the maintenance of CDR configuration were determined (linear positions adjacent to CDR antigen binding site or amino acid residues located within 6 Å away from CDR); various combinations of sequences of humanized heavy chain variable region (SEQ ID No.15 and SEQ ID No.16) were designed.

Similarly, the sequence of murine anti-CD20 antibody 2B8 VL was analyzed, VL FR1, FR2, FR3 and FR4 were compared with sequence database of human antibody gene (NCBI Ig BLAST) so as to identify, corresponding sequences of human germline antibody variable region which are similar to the sequences of FR1, FR2, FR3 and FR4 of light chain variable region of murine antibody 2B8. And then the binding affinity of said sequence with HLA-DR molecule was analyzed by in-silicon analysis. The framework sequences with lowest affinity were identified, and finally, the humanized sequences of FR1, FR2, FR3 and FR4 of light chain variable region were respectively determined as SEQ ID No. 18, SEQ ID No, 21, SEQ ID No, 22, SEQ ID No.23 and SEQ ID No. 32. Based on the structure of such framework, an in-silicon molecular modeling was used to analyze the stereo structure of variable region of murine 2B8 anti-CD20 antibody; and then the corresponding framework amino acid residues of murine 2B8 necessary for the maintenance of CDR configuration were determined (linear positions adjacent to CDR antigen binding site or amino acid residues located within 6 Å away from CDR); various combinations of sequences of humanized light chain variable region (SEQ ID No.34 and SEQ ID No.35) were designed.

On such a basis, molecular docking method can be used to analyze the stereo binding of the epitope of CD20 ($^{170}$ANPS$^{173}$) and its surrounding amino acid residues $^{168}$E, $^{169}$P, $^{174}$E and $^{175}$K to humanized heavy chain variable region. By calculating static electricity, salvation, Van der Waals force and entropy, the amino acids in sequence of CDR1, CDR2 and CDR3 can be optimized to improve the binding of CDR region to CD20 antigenic epitope, and thus obtain antibody with better activity. Preferably, the heavy chain variable region has the following sequence:

(Seq ID No: 36)
QVQLVQSGAEVKKPGASVKVSCKASGYTFTSYTMHWVRQAPGKGLEWIGAIYPGNSDTNYNQKFKGRVTITADKSTSTA

YMELSSLRSEDTAVYYCARSTYYGGDWNFEVWGQGTTVTVSS,
FIG. 10, hVH-2).

Similarly; the stereo structure analysis indicated that the CDR1 and CDR2 of humanized. LC do not directly bind to the antigenic epitope of CD20, Only CDR3 of humanized LC together with CDR1, CDR2 and CDR3 of HC form binding pocket of epitope of CD20 ($^{170}$ANPS$^{173}$). Thus, only CDR3 of LC was optimized. The light chain variable region of antibody has the following sequence:

(Seq ID No: 37)
DVVMTQSPAFLSVTPGEKVTITCRASSSVSYIHWFQQKPCKAPKPLIYATSNLASGVPSRFSGSGSGTDFTLTINSLEA

EDAATYYCQQWTSKPPTFGGGTKVEIK,
FIG. 11, hVK-2).

The resulting humanized antibodies according to present invention posses the following combination:

TABLE 1

Combinations of humanized anti-CD20 antibodies

| Antibody | VH SEQ ID | Vκ SEQ ID |
|---|---|---|
| 1534 | 15 | 34 |
| 1634 | 16 | 34 |
| 1535 | 15 | 35 |

TABLE 1-continued

Combinations of humanized anti-CD20 antibodies

| Antibody | VH SEQ ID | Vκ SEQ ID |
|---|---|---|
| 1635 | 16 | 35 |
| 3637 | 36 | 37 |

These humanized anti-CD20 antibodies have the activity of binding to CD20, and have the activity for inducing ADCC, CDC and inducing the apoptosis of CD20 positive malignant B cells (see examples).

The constant region of heavy chain was derived from human IgG1, and the constant region of light chain was derived from human κ chain, both were from normal human B lymphocytes. The full length gene of HC and LC of antibody were generated by connecting variable region to constant region by using genetic engineering (overlap extension PCR). The DNA sequence encoding a humanized anti-CD20 can be recombined to construct vector for transcription and expression in mammalian cells. The expression vector according to present invention comprises DNA sequences encoding both variable region and constant region of heavy and light chain from human derived anti-CD20 mAb. However, two expression vectors can be constructed respectively, one comprises heavy chain variable and constant regions, and the other comprises light chain variable and constant regions. Mammalian cells were transfected with both vectors simultaneously. The expression vector further comprises a promoter and DNA sequence encoding secretion signal peptide, as well as at least one drug resistance gene for screening. The methods as used include DNA synthetic techniques and in vitro recombinant techniques. The vector suitable for the present invention can be viral or nonviral. Preferable a viral vector includes an adenovirus, AAV, herpes simplex virus, lentivirus and retrovirus vectors. Nonviral vector is a plasmid.

2. Methods for Preparation of Antibodies

Methods for producing recombinant antibodies comprise (i) linearizing the expression vector which comprises the DNA sequence encoding the humanized anti-CD20 MAb according to present invention, (ii) transfecting mammalian cells with said linearized vector, in which the light and heavy chains can be co-transfected into a single cell by using separate vectors or by using a single expression vector that contains the coding genes for both the light and heavy chain, (iii) selecting transfected cells which express drug resistance gene, and (iv) separating the cells which secret the humanized anti-CD20 mAb according to the present invention. In particular, the nucleotides encoding the antibody according to present invention may be directly introduced into a host cell, and the cell can be incubated under conditions which are sufficient to induce expression of the encoded antibody. Any cell suitable for expression may be used as a host cell. For example, cells from yeast, insect, plant, etc.

In particular, a mammalian cell line that generally does not produce antibodies is used, such as Chinese hamster ovary (CHO) cells, NS0 cells, SP2/0 cells, Cos-7 cells and other mammalian cells such as PER.C6 cells. Suitable methods include electroporation, lipofactemine, gene gun technology; calcium phosphate precipitation, direct microinjection and the like. The choice of method is generally dependent on the type of cell to be transformed and on the circumstances under which the transformation takes place.

For long-term, high-yield production of recombinant antibodies, stable expression may be used. The drug resistance gene in recombinant plasmid makes it possible to screen cell colonies that can be cloned, wherein plasmid has been stably integrated into chromosome.

During the culturing of cells, the transformed cells are cultured in a series of bioreactors to amplify the cells which is inoculated. Anti-CD20 antibodies are produced and accumulated in culture. During cultivation phase, the transfected cells are cultured, according to methods known in the art, in a liquid medium containing similar carbon source (carbohydrates such as glucose or lactose), nitrogen source (amino acids, peptides, proteins or their degradation products such as peptones, ammonium salts and the like), and inorganic salts (sulfates, phosphates and/or carbonates of sodium, potassium, magnesium and calcium). The cultivation medium preferably includes a conventional nutrient medium such as Dulbecco's Modified Eagle's Medium (DIEM) (Sigma), Ham's F10 (Sigma), Minimal Essential Medium (MEM) (Sigma), RPMI-1640 (Sigma) or NCTC-135. When necessary, any of these media can be supplemented with amino acids (such as glutamine), hormones or other growth factors (insulin, transferrin, or epidermal growth factor), buffers, nucleotides, ionic surfactants, and glucose or equivalent energy source. The medium can further contain trace elements that promote growth, such as iron chelates (eg., chelate B, invitrogen Corp., Carlsbad, Calif.) and manganese. During the cultivation phases, culture conditions, such as temperature, pH, and the like, should be monitored to ensure rapid cell growth.

The obtained antibody molecule of the invention may be purified by any method known in the art. For example, the antibody molecule of the invention can be purified by Protein A affinity chromatography as well as ion exchange chromatography, or by any other standard technique for the purification of proteins.

3. Formulations

The antibodies according to present invention can be formulated into formulation using one or more pharmaceutically acceptable excipient by conventional methods. The term "pharmaceutically acceptable excipient" means one or more organic or inorganic, natural or synthetic ingredients which in combination with antibody can improve its stability, as well as carriers for clinical application. Suitable carrier includes pharmaceutically acceptable sterile saline and aqueous and non-aqueous isotonic sterile solutions and sterile suspension known to those skilled in the art. The antibodies of the present invention, especially the formulation consisting of 150 mM NaCl, 25 mM sodium citrate at pH6.5, dehydrated sodium glycyrrhizinate, 0.05% Polysorbate 80 provides outstanding stability.

4. Dosage and Mode of Administration

An effective amount can be determined depending on the individual. The symptoms to be treated and the effect should be, to some extent, taken into consideration. An effective amount can be determined by standard pharmaceutical procedures of in vitro cell cultures or experimental animals, e.g., determining the $LD_{50}$ (median lethal dose) and $ED_{50}$ (median effective dose). The therapeutic index refers to the ratio of toxic dose to therapeutic dose, and can be expressed as $LD_{50}/ED_{50}$. Therapeutic regime that exhibits higher therapeutic index is preferred. The data obtained from in vitro cell culture assays and animal studies can be used to determine the dosage for human use. Exemplary dosage includes but is not limited to the range of 0.5 mg/kg to 100 mg/kg. Preferably, the dosage for treatment is present within a range of low toxicity or no toxicity $ED_{50}$ plasma concentration. Such a range, depending upon the dosage form and the route of administration, may vary. For a therapeutic regime, the therapeutically effective dosage may be determined in animal models by estimating peripheral circulatory plasma concentration range for more accurate determination of effective dosage in humans.

The antibodies of the present invention may be administered in any pharmaceutically acceptable manner. This may include injection via parenteral routes such as intravenous, intraarterial, subcutaneous, intramuscular, intratumor, intraperitoneal, intraventricular, intraepidural, or by catheter (via blood vessels which supply local tumors); or sustained release administration from body surface.

5. Clinical Therapeutic Application

The humanized anti-CD20 antibodies according to present invention are used as the main component for the treatment of diseases caused by B cell abnormality, particularly non-Hodgkin's lymphoma, chronic lymphatic leukemias, acute lymphatic leukemias, and Waldenstrom's macroglobulinemia, as well as various autoimmune diseases, such as immune-mediated thrombocytopenias, e.g. acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, rheumatoid arthritis, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy; amyotrophic lateral sclerosis, tabes dorsalis, giant cell arteritis/polymyalgia, pernicious anemia, rapidly progressive glomerulonephritis and fibrosing alveolitis.

The compositions for treatment comprise at least anti-CD20 antibody alone or in combination with other therapeutic agents such as chemotherapy or immunomodulators.

The antibodies of the present invention can also be derived antibodies, including monovalent antibody, multivalent antibody or single chain antibody.

The antibodies of the present invention can also be modified antibody, including the improvement in Fc fragment for enhancement of the function of effector. For example, the substitution or glycosylation of one or more amino acids in Fc region may enhance the function of effector and thus enhance antibody dependent cell-mediated cytotoxicity and/or complement dependent cytotoxicity. Fc fragment can also be conjugated with radioisotope, chemotherapy drug or toxin, and thus enhances antibody cytotoxicity.

The present invention provides humanized anti-CD20 antibodies with reduced human immunogenicity but maintaining enhanced therapeutic effect. The present invention provides safe and effective drugs for treatment of B cell malignancy and various autoimmune diseases associated with B cell.

BRIEF DESCRIPTION OF THE DRAWINGS

FIG. 1. Human germline FR1 sequence corresponding to FR1 sequence of murine antibody 2B8 heavy chain variable region:
SEQ. ID. No. 1 (2B8 HC).
SEQ. ID. No. 2 (IGHV7-4-1*03, IGHV7-4-1*02, and IGHV7-4-1*01),
SEQ. ID. No. 3 (IGHV1-8*01, IGHV1-3*01, IGHV1-2*04, IGHV1-46*03, IGHV1-2*02, IGHV1-2*01, and IGHV1-46*01).

FIG. 2. Human germline FR2 sequence corresponding to FR2 sequence of murine antibody 2B8 heavy chain variable region:
SEQ. ID. No. 4 (2B8 HC),
SEQ. ID. No. 5 (IGHV4-55*09, IGHV4-55*08, IGHV4-55*06. IGHV4-55*02, IGHV4-55*01, and IGHV4-55*05),
SEQ. ID. No. 6 (IGHV3-72*02 IGHV3-72*01, and IGHV3-71*01).

FIG. 3. Human germline FR3 sequence corresponding to FR3 sequence of murine antibody 2B8 heavy chain variable region:
SEQ. ID. No. 7 (2B8 HC),
SEQ. ID. No. 8 (IGHV1-69*10, IGHV1-69*09, IGHV1-69*06, IGHV1-69*04, IGHV1-69*08, and IGHV1-69*02),
SEQ. ID. No. 9 (IGHV1-69*12, IGHV1-69*11, IGHV1-69*01, and IGHV1-69*13).

FIG. 4. Human germline FR4 sequence corresponding to FR4 sequence of murine antibody 2B8 heavy chain variable region:
SEQ. ID. No. 10 (2B8 HC),
SEQ. ID. No. 11 (JH1, JH4, and JH5),
SEQ. ID. No. 12 (JH2),
SEQ. ID. No. 13 (JH3),
SEQ. ID. No. 14 (JH6).

FIG. 5. Human germline FR1 sequence corresponding to FR1 sequence of murine antibody 2B8 light chain variable region:
SEQ. ID. No. 17 (2B8 LC),
SEQ. ID. No. 18 (IGKV6D-41*01),
SEQ. ID. No. 19 (IGKV3D-20*01, IGKV3-NL5*01, IGKV3-20*02, IGKV3-11*02, IGKV3-NL4*01, IGKV3-11*01, IGKV3D-11*01, IGKV3-NL2*01, and IGKV3-NL1*01).

FIG. 6. Human germline FR2 sequence corresponding to FR2 sequence of murine antibody 2B8 light chain variable region:
SEQ. ID. No. 20 (2B8 LC),
SEQ. ID. No. 21 (IGKV1-16*02, and IGKV1-16*01),
SEQ. ID. No. 38 (IGLV2-5*02, and IGKV2-5*01),
SEQ. ID. No. 39 (IGKV7-43*01),
SEQ. ID. No. 40 (IGKV7-46*02, and IGKV7-46*01).

FIG. 7. Human germline FR3 sequence corresponding to FR3 sequence of murine antibody 2B8 light chain variable region:
SEQ. ID. No. 22 (2B8 LC),
SEQ. ID. No. 23 (IGKV6D-21*01 and IGKV6-21*01),
SEQ. ID. No. 24 (IGKV6D-41*01),
SEQ. ID. No. 25 (IGKV3-20*02),
SEQ. ID. No. 26 (IGKV3-NL3*01),
SEQ. ID. No. 27 (IGKV1D-43*01 and IGKV1-NL1*01).

FIG. 8. Human germline FR4 sequence corresponding to FR4 sequence of murine antibody 2B8 light chain variable region:
SEQ. ID. No. 28 (2B8 LC),
SEQ. ID. No. 29 (JK1),
SEQ. ID. No. 30 (JK2),
SEQ. ID. No. 31 (JK3),
SEQ. ID. No. 32 (JK4),
SEQ. ID. No. 33 (JK5).

FIG. 9. Sequences of humanized anti-CD20 antibodies heavy chain variable region, 9A, 9B; Sequences of humanized anti-CD20 antibodies light chain variable region, 9C, 9D; 9A, 9B, 9C and 9D correspond to SEQ ID NO:15, SEQ ID NO:16, SEQ ID NO:34, SEQ ID NO:35, respectively.

FIG. 10. The optimized CDR sequence of humanized anti-CD20 antibody heavy chain variable region, SEQ ID NO: 16 and 36.

FIG. 11. The optimized CDR sequence of humanized anti-CD20 antibody light chain variable region, SEQ ID NO: 35 and 37.

FIG. 12. Specific binding of anti-CD20 humanized mAb to CD20+ Ramos lymphoma, but not CD20− T-cell leukemia Jurkat cell. FIG. A: Ramos lymphoma cell; FIG. B: Jurkat leukemia cell.

DESCRIPTION OF EMBODIMENTS

Figure 13:
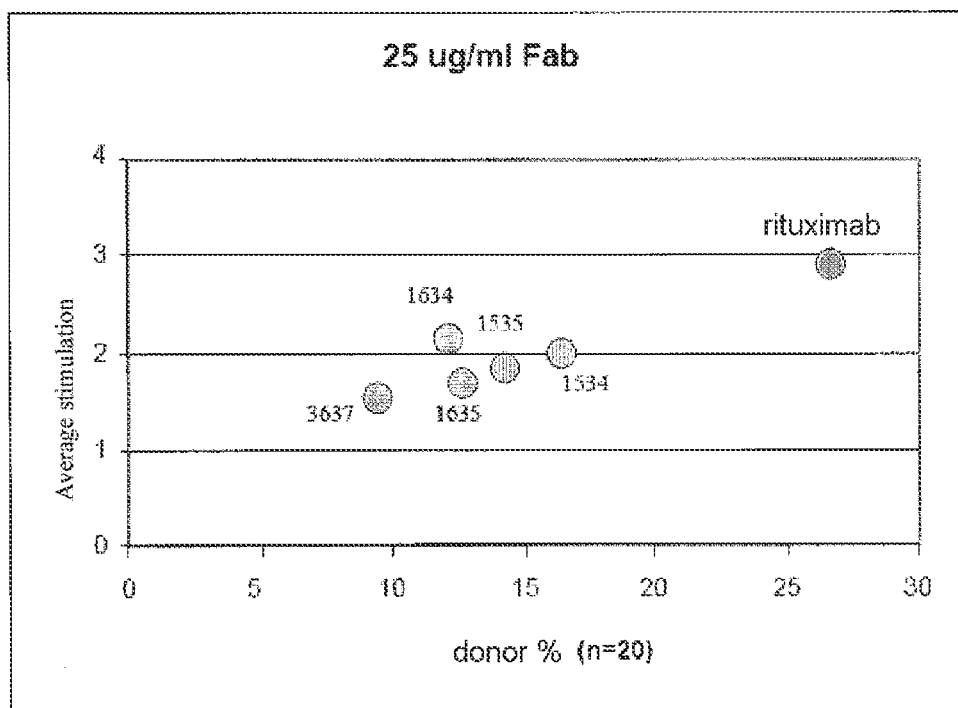
FIG. 13. In vitro immunogenicity test of humanized anti-CD20 antibody using dendritic cell (DC)-T cell stimulation assay (n=20).

1. Designing Framework Sequence of Humanized Anti-CD20 Murine 2B8 Antibody HC Variable Region The following is sequence of HC variable region of murine anti-CD20 antibody 2B8, the underlined portion shows the sequence of murine antibody framework:

<u>QVQLQQPGAELVKPGASVKMSCKASGYTFT</u>SYNMH<u>WVKQTPGRGLEWIG</u>AIYPGNGDTSYNQKFKG

<u>KATLTADKSSTAYMQLSSLTSEDSAVYYCAR</u>STYYGGDWYFNV<u>WGAGTTVTVSA</u>

After comparing sequence of FR1, FR2, FR3 and FR4 of HC variable region of murine anti-CD20 antibody 2B8 with sequence database of human antibody genes (NCBI Ig BLAST), corresponding sequences of FR1, FR2, FR3 and FR4 of human germline antibody variable region (which have much lower immunogenicity than mature antibody) which are similar to the sequences of FR1, FR2, FR3 and FR4 of HC variable region of murine antibody 2B8 are identified.

FIG. 1 shows the FR1 sequence of human germline antibody variable region corresponding to FR1 sequence of murine antibody 2B8 heavy chain variable region (Seq ID No: 1, QVQLQQPGAELVKPGASVKMSCKASGYTFT), the ten resulting human germline antibodies with similar FR1 sequences have two distinct sequences as below:

```
                                      Seq ID No: 2
QVQLVQSGSELKKPGASVKVSCKASGYTFT

Seq ID. No: 3
QVQLVQSGAEVKKPGASVKVSCKASGYTFT
```

The binding affinity of said sequences to HLA-DR molecules, mainly including HLA-DR B1-0101, HLA-DR B1-0301, HLA-DR B1-0401, HLA-DR B1-0701, HLA-DR B1-1101, HLA-DR B1-1301, HLA-DR B1-1501, was done by in silicon analysis. The sequence of original murine FR1 (Seq ID NO: 1) has three potential HLA-DR binding sites, humanized sequence Seq ID No: 2 has two potential HLA-DR binding sites, while humanized sequence Seq ID No: 3 has only one potential HLA-DR binding site. Therefore, Seq ID No: 3 having lower affinity was selected as the framework sequence of humanized HC variable region FR1.

Similarly, FIG. 2 shows the FR2 sequence of human germline antibody variable region corresponding to FR2 sequence of murine antibody heavy chain variable region (Seq ID No: 4, WVKQTPGRGLEWIG), the ten resulting human germline antibodies with similar FR2 sequences have two distinct sequences as below:

```
                                      Seq ID No: 5
WVRQPPGKGLEWIG

Seq ID No: 6
WVRQAPGKGLEWVG
```

And then the binding affinity of said sequences to HLA-DR molecules was analyzed by in silicon analysis. The affinity of both Seq ID NO: 5 and Seq ID NO: 6 was lower than that of murine FR2 sequence. Seq ID NO: 5 or Seq ID NO: 6 having lower affinity was selected as the framework sequence of humanized HC variable region FR2.

Similarly, FIG. 3 shows the FR3 sequence of human germline antibody variable region corresponding to FR3 sequence of murine antibody 2B8 heavy chain variable region (Seq ID No: 7, KATLTADKSSSTAYMQLSSLTSEDSAVYYCAR), the ten resulting human germline antibodies with similar FR3 sequences have two distinct sequences, these two sequences are:

```
                                      Seq ID No: 8
RVTITADKSTSTAYMELSSLRSEDTAVYYCAR

Seq ID No: 9
RVTITADESTSTAYMELSSLRSEDTAVYYCAR
```

And then the binding affinity of said sequences to HLA-DR molecules was analyzed by in silicon analysis. The affinity of both Seq ID NO: 8 and Seq ID NO: 9 were lower than that of murine FR3 sequence. Seq ID NO: 8 and Seq ID NO: 9 having lower affinity were selected as the framework sequence of humanized HC variable region FR3.

Similarly, FIG. 4 shows the FR4 sequence of human germline antibody variable region corresponding to FR4 sequence of murine antibody 2B8 heavy chain variable region (Seq ID No: 10, WGASTTVTVSA), the six resulting human germline antibodies with FR4 sequences have 3 distinct sequences, these 3 sequences are:

```
                                      Seq ID No: 11
WGQGTLVTVSS

Seq ID No: 12
WGRGTLVTVSS

Seqe ID No: 13
WGQGTMYTVSS

Seq ID No: 14
WGQGTTVTVSS
```

And then the binding affinity of said sequences to HLA-DR molecules was analyzed by in silicon analysis. Seq ID NO: 14 having lower affinity was selected as the framework sequence of humanized HC variable region. FR4.

Two sequences of humanized antibody HC variable regions were designed based on the optimization of framework sequence: (FIGS. 9A, 9B):

(Seq ID No: 5; refers to Seq ID No: 9)
QVQLVQSGAEVKKPGASVKVSCKASGYTFTSYNMHWVRQPPGKGLEWIG

AIYPGNGDTSYNQKFKGRVTITADESTSTAYMELSSLRSEDTAVYYCAR

STYYGGDWYFNVWGQGTTVTVSS (Seq ID No: 16, refers to Seq ID No: 8)
QVQLVQSGAEVKKPGASVKVSCKASGYTFTSYNMHWVRQAPGKGLEWIG

AIYPGNGDTSYNQKFKGRVTITADKSTSTAYMELSSLRSEDTAVYYCAR

STYYGGDWYFNVWGQGTTVTVSS

2. Designing Framework Sequence of Humanized Anti-CD20 Murine 2B8 Antibody LC Variable Region The following is sequence of LC variable region of murine anti-CD20 antibody 2B8, in which the underlined portion shows the sequence of murine antibody framework:

QIVLSQSPAILSASPGEKVTMTCRASSSVSYIHWFQQKPGQQKPGSSPKPWIYATSNLASGVPVRFSGSGS

GTSYSLTISRVEAEDAATYYCQQWTSNPPTFGGGTKLEIK

After comparing sequence of FR1, FR2, FR3 and FR4 of LC variable region of murine anti-CD20 antibody 2B8 with sequence database of human antibody genes (NCBI Ig BLAST), corresponding sequences of FR1, FR2, FR3 and FR4 of human germline antibody variable region which are similar to the sequences of FR1, FR2, FR3 and FR4 of LC variable region of murine antibody 2B8 are identified.

FIG. 5 shows the FR1 sequence of human germline antibody variable region corresponding to FR1 sequence of murine antibody 2B8 light chain variable region (Seq ID No: 17, QIVLSQSPAILSASPGEKVTMTC), the ten resulting human germline antibodies with FR1 sequences have two distinct sequences as below:

Seq ID No: 18
DVVMTQSPAFLSVTPGEKVTITC

Seq ID No: 19:
EIVLTQSPATLSLSPGERATLSC

The binding affinity of said sequences to HLA-DR molecules, including HLA-DR B1-0101, HLA-DR B1-0301, HLA-DR B1-0401, HLA-DR B1-0701, HLA-DR B1-1101, HLA-DR B1-1301, HLA-DR B1-1501, was analyzed by in silicon analysis. The sequence of original murine FR1 (Seq ID NO: 17) has 4 potential HLA-DR binding sites, humanized sequence Seq ID No: 18 and humanized sequence Seq ID No: 19 have significantly lower affinity at potential HLA-DR binding sites. Therefore, Seq ID No: 18 having lower affinity was selected as the framework sequence of humanized LC variable region FR1.

Similarly, FIG. 6 shows the FR2 sequence of human germline antibody variable region corresponding to FR2 sequence of murine antibody 2B8 light chain variable region (Seq ID No: 20, WFQQKPGSSPKPWIY), the 7 resulting human germline antibodies with FR2 sequences have 4 distinct sequences as below:

Seq ID No: 21
WFQQKPGKAPKSLIY

Seq ID No: 38
WYQQPGTVPKPMIY

Seq ID No: 39
WFQQKPGQAPRALIY

Seq ID No: 40
WFQQKPGQAPRTLIY

And then the binding affinity of said sequences to HLA-DR molecules was analyzed by in silicon analysis. The affinity of both Seq ID NO: 21 and Seq ID NO: 28 were lower than that of murine FR2 sequence. Seq ID NO: 21 having lower affinity was selected as the framework sequence of humanized LC variable region FR2.

Similarly, FIG. 7 shows the FR3 sequence of human germline antibody variable region corresponding to FR3 sequence of murine antibody 2B8 light chain variable region No: 22, GVPVRFSGSGSGTSYSLTISRVEAEDAATYYC), the 7 resulting FR3 sequences of human germline antibody have 5 distinct sequences as below:

Seq ID No: 23
GVPSRFSGSGSGTDFTLTINSLEAEDAATYYC

Seq ID No: 24
GVPSRFSGSGSGTDFTFTISSLEAEDAATYYC

Seq ID No: 25
GIPARFSGSGSGTDFTLTISRLEPEDFAVYYC

Seq ID No: 26
GIPARFSGSGSGTDFTLTISRLQSEDFAVYYC

Seq ID No: 27
GVPSRFSGSGSGTDYTLTISSLQPEDFATYYC

And then the binding affinity of said sequences to HLA-DR molecules was analyzed by in silicon analysis. Seq ID NO: 23 having lower affinity was selected as the framework sequence of humanized LC variable region FR3.

Similarly, FIG. 8 shows the FR4 sequence of human germline antibody variable region corresponding to FR4 sequence of murine antibody 2B8 light chain variable region (Seq ID No: 28, WGAGTTVTVSA), the 5 resulting human germline antibodies with FR4 sequences have 5 distinct sequences as below:

Seq ID No: 29
FGQGTKVEIK

Seq ID No: 30
FGQGTKLEIK

Seq ID No: 31
FGPGTKVDIK

Seq ID No: 32
FGGGTKVEIK

Seq ID No: 33
FGQGTRLEIK

And then the binding affinity of said sequences to HLA-DR molecules was analyzed by in silicon analysis. Seq TD NO: 32 having lower affinity was selected as the framework sequence of humanized LC variable region FR4.

The sequence of humanized antibody LC variable region was designed based on the optimization of framework sequence: (FIG. 9C):

(Seq ID No: 34)
DVVMTQSPAFLSVTPGEKVTITCRASSSVSYIHWFQQKPGKAPKSLIYATSNLASGVPSRFSGSGSGTDFTLTINSLEAEDAATYYCQQWTSNPPTFGGGTKVEIK

On such a basis, in-silicon molecular modeling (Swiss-PdbViewer) analysis is used to analyze the stereo structure of variable region of murine 2B8 anti-CD20 antibody. The result shows that amino acid residue P at position 44 supports CDR configuration, the maintenance of amino acid residue P will facilitate the structure of CDR (FIG. 9D).

(Seq ID No: 35)
DVVMTQSPAFLSVTPGEKVTITCRASSSVSYIHWFQQKPGKAPKPLIYATSNLASGVPSRFSGSGSGTDFTLTINSLEAEDAATYYCQQWTSNPPTFGGGTKVEIK

On such a basis, molecular docking method can be used to analyze the stereo binding of the epitope of CD20 ($^{170}$ANPS$^{173}$) and its surrounding amino acid residues $^{168}$E, $^{169}$P, $^{174}$E and $^{175}$K to humanized heavy chain variable region. By calculating static electricity, salvation, Van der Waals force and entropy, the amino acids in sequence of CDR1, CDR2 and CDR3 can be optimized to improve the binding of CDR region to CD20 antigenic epitope, and thus obtain antibody with better activity. The heavy chain variable region of antibody has the following sequence:

(Seq ID No: 36)
QVQLVQSGAEVKKPGASVKVSCKASGYTFTSYTMHWVRQAPGKGLEWIGAIYPGNSDTNYNQKFKGRVTITADKSTSTAYMELSSLRSEDTAVYYCARSTYYGGDWNFEVWGQGTTVTVSS,
(FIG. 10 hVH-2).

Based on the same reason, stereo structure analysis indicated that the CDR1 and CDR2 of humanized LC were not directly bind to the antigenic epitope of CD20. Only CDR3 of humanized LC together with CDR1, CDR2 and CDR3 of HC form binding pocket of epitope of CD20 ($^{170}$ANPS$^{173}$). Thus, only CDR3 of LC was optimized. The light chain variable region of antibody has the following sequence:

(Seq ID No: 37)
DVVMTQSPAFLSVTPGEKVTITCRASSSVSYIHWFQQKPGKAPKPLIYATSNLASGVPSRFSGSGSGTDFTLTINSLEAEDAATYYCQQWTSKPPTFGGGTKVEIK,
(FIG. 11, hVK-2).

The resulting humanized antibodies according to present invention posses the following combination:

TABLE 1

Combinations of humanized anti-CD20 antibodies

| Antibody | VH SEQ ID | Vκ SEQ ID |
|---|---|---|
| 1534 | 15 | 34 |
| 1634 | 16 | 34 |
| 1535 | 15 | 35 |
| 1635 | 16 | 35 |
| 3637 | 36 | 37 |

3. Preparation of Anti-CD20 Humanized mAb

According to the HC and LC sequence of humanized antibodies shown in Table 1, oligonucleotides fragments of PCR primers for HC and LC variable regions were designed and synthesized. Oligonucleotides fragments of PCR primers are about 54 bases in length with about 18 bases overlap. Equal amount of each primer were mixed together and used for overlap extension PCR reaction.

PCR reaction system: dNTPs 0.2 µM (final concentration); each PCR primer 1 µl; 10×buffer 3 µl; cloned pfu (Invitrogen) 1 µl; $H_2O$ was added to 30 µl.

PCR reaction condition: 94° C. 3 min→(94° C. 30 s→56° C. 30 s→72° C. 1 min)×30→72° C. 10 min.

PCR product was isolated and recovered using 1% agarose gel electrophoresis, and was further cloned into vector pCR-BluntII-TOPO (Invitrogen) after EcoRI digestion. After transformation into TOPO10 (Invitrogen), 10 colonies were selected from LB/Kanamycin plate and further inoculated into LB liquid culture medium containing Kanamycin. The plasmid was extracted using QIAGEN plasmid extraction kit (QiAquick PCR purification kit), and then the sequences of HC and LC variable region were confirmed by sequencing.

4. Construction of Vectors

RNA was isolated form normal human B cells. The Fc fragment of recombinant human constant region of heavy chain and κ fragment of recombinant human constant region of light chain were generated by PCR, and then they were constructed into the pcDNA3.1 (invitrogen) expression vector. After transformed into DH5α, the plasmid was extracted and the sequence was confirmed by sequencing. The HC variable region was obtained from pCR-BluntII-TOPO positive clone by Eco47III/NheI digestion and cloned into pcDNA3.1-Fc expression vector. The LC variable region was obtained from pCR-BluntII-TOPO positive clone by AscI/BsiWI digestion and cloned into the pcDNA3.1-κ expression vector. After transformed into DH5α, the plasmid was extracted and the positive clones were determined. The result of sequencing was consistent with the sequence encoding the antibodies shown in Table 1.

5. Transfection of CHO and Selection of Positive Clones

Cell line and culture condition: CHO-S cells (Invitrogen) were cultivated in 1×CD-CHO (GIBCO), 1×HT (GIBCO), 8 mM glutamine (GIBCO), at 37° C., in incubator with 8% $CO_2$.

According to the instruction of manufacturer, transfection of CHO-S was done by using DMRIE-C transfection kit (Invitrogen). Three days after transfection, 500 µg/ml G418 (GIBCO) and 12.5 µg/ml purimycin (Sigma) were added to the above culture medium for the purpose of pressure screening. 14 days after pressure screening, single clones were picked. Positive clones were selected by direct competitive ELISA. The selected positive clones were transferred to 6-well plate at $2.5 \times 10^5$ cells/ml and cultivated for four more days. And then the number of each clone was detected, the yield of antibody was measured by direct competitive ELISA. The production rate was calculated as the following formula: pg/cell/day=$10^9$×µg/ml (from ELISA, =mg/L) (Days in culture)×(Day 0 seeded via cells/ml+Day 3-4 harvested via cells/ml)/2)×1000. After comparing the production rate of each clone, the clone having the highest production rate was selected for further scale-up culture. The humanized anti-CD20 antibodies were purified from the cell culture supernatant by protein A affinity column.

6. Assay of Antibody Specificity by FACS

The specific binding to CD20 was detected by using CD20+ Ramos cell (ATCC) and T lymphocyte leukemia Jurkat cell (ATCC). Cells were incubated with various concentration of antibodies for 1 hour at 4° C. After washing with PBS for 3 times, 1:100 diluted FITC labeled anti-human Fc γ specific second antibody (The Jakson Laboratory) was added and incubated for 1 h at 4° C. After washing with PBS for three times, specific binding was analyzed by FACS instrument. As shown in FIG. 12, the humanized anti-CD20 antibody 1534, 1634, 1535, 1635, 3637 according to present invention were able to specifically bind CD20+ B Ramos cells instead of CD20-T leukemia Jurkat cells. The clone 3637 has further enhanced binding to antigen (FIG. 12).

7. In Silicon In Vitro Immunogenicity Assay

The immunogenicity of antibody was studied by analyzing the binding affinity of humanized anti-CD20 antibodies according to present invention to HLA-DR molecule using in silicon method (such as NetMHCIIpan or self-designed program), and by comparing the antibodies according to present invention with those chimeric antibodies and other humanized anti-CD20 antibodies mentioned in the Section of Background. The studied anti-CD20 antibody HC has high binding affinity sites (binding affinity<100 nM). The sequences were shown in Table 2.

TABLE 2

The binding affinity of humanized anti-CD20 antibodies HC with HLA DR

| HC of antibody | sequence | affinity (nM) |
|---|---|---|
| 1534, 1535, 1634, 1635 | YMELSSLRS | 20.57 |
| | YFNVWGQGT | 88.72 |
| 3637 HC | YMELSSLRS | 20.57 |
| hA20VH2 | VRQAPGQGL | 76.88 |
| | LEWMGAIYP | 71.79 |
| | YMELSSLRS | 20.57 |
| H1286 | VRQAPGQGL | 76.88 |
| | FKGKATITA | 69.29 |
| | YMELSSLRS | 20.57 |
| Rituximab | LQQPGAELV | 67.68 |
| | VKPGASVKM | 71.22 |
| | VKQTPGRGL | 81.66 |
| | FKGKATLTA | 64.52 |
| | YMQLSSLTS | 16.57 |
| | YFNVWGAGT | 72.34 |

The HC of chimeric rituximab contains 6 potential high affinity binding sites with HLA-DR (Kd<100 nM). The HC of humanized anti-CD20 antibody hA20VH2 (Immunomedics, Inc.) and H1286/L373 (VACCINEX) contain 3 potential high affinity binding sites with HLA-DR (Kd<100 nM). However, the FTC of humanized anti-CD20 antibodies 1534, 1535, 1634, 1635 according to present invention contain only 2 potential high affinity binding site, the binding site of 3637 was further reduced to only one. Thus the immunogenicity generated by the heavy chain of humanized anti-CD20 antibody according to present invention was significantly reduced when compared with that of chimeric antibodies and other humanized anti-CD20 antibodies mentioned in the Section of Background.

The studied anti-CD20 antibody LC has high binding affinity sites (binding affinity<100 nM). The sequences were shown in Table 3.

| antibody | sequence | affinity (nM) |
|---|---|---|
| 1534, 1535, 1634, 1635 | VMTQSPAFL | 46.11 |
|  | MTQSPAFLS | 35.89 |
|  | LIYATSNLA | 39.67 |
|  | IYATSNLAS | 53.45 |
| 3637 | VMTQSPAFL | 46.11 |
|  | MTQSPAFLS | 35.89 |
|  | LIYATSNLA | 39.67 |
|  | IYATSNLAS | 53.45 |
| hA30VK | LTQSPSSLS | 36.95 |
|  | WIYATSNLA | 34.84 |
|  | IYATSNLAS | 73.45 |
|  | LASGVPVRF | 76.15 |
| L373 | MTQSPSSLS | 50.14 |
|  | LIYAASSLQ | 67.47 |
|  | IYAASSLQS | 71.96 |
|  | LQSGVPSRF | 80.28 |
|  | YTLTISSLG | 91.97 |
| Rituximab | IVLSQSPAI | 79.06 |
|  | VLSQSPAIL | 67.87 |
|  | LSQSPAILS | 27.23 |
|  | LSASPGEKV | 72.8 |
|  | WIYATSNLA | 31.84 |
|  | IYATSNLAS | 73.45 |
|  | LASGVPVRF | 76.15 |

The LC of chimeric rituximab contains 7 potential high affinity binding sites with HLA-DR (Kd<100 nM). The LC of humanized anti-CD20 antibody H1286/L373 (VACCINEX) contain 5 potential high affinity binding sites; hA20VK (Immunomedics, Inc.) contains 4 high affinity binding sites. However, although the LC of humanized anti-CD20 antibodies 1534, 1535, 1634, 1635 and 3637 according to present invention contain 4 binding sites, the affinity was lower than that of hA20VK. Thus the immunogenicity generated by the light chain of humanized anti-CD20 antibody according to present invention was significantly reduced when compared with that of chimeric rituximab, and was further reduced when compared with that of other humanized anti-CD20 antibodies mentioned in the Section of Background.

8. In Vitro Immunogenicity Test Using Dendritic Cell (DC)-T Cell Stimulation Assay Blood from normal volunteers (n=20) was collected in heparinized syringes and mixed with equal volume of $Ca^{2+}$/$Mg^{2+}$ free HBSS (Life Technologies). Samples were subjected to lymphoprep gradient (Life Technologies) for separation and then centrifuged at 800 g for 30 min. PBMC located at the interface were harvested and washed in HEPES buffered saline and re-suspended in medium (RPMI 1640 medium (Life Technologies)). In order to get monocytes, the PBMC were cultivated for 2 hours in serum-free AIM V media (Gibco) supplemented with 1:100 dilution of beta-mercaptoethanol. Then the monocytes were cultivated for another 5 days after adding 800 units/ml of GM-CSF (Endogen) and 500 units/ml of IL-4 (Endogen), followed by 2-day cultivation after adding 0.2 units/ml of TNFα (Endogen) and IL-1α at a final concentration of 50 units/ml (Endogen). On day 7, 50 mg/ml of Mitomycin C was added for 1 hour to terminate the differentiation of dendritic cells, Those mature dendritic cells were harvested by centrifugation at 600 g. Then, cells were inoculated onto round-bottomed 96-well plates at $2 \times 10^4$ cells/well (100 µl). CD4+ T cells were subjected to negative selection using the CD4+ Cellect Kit (Biotex): PBMC were suspended in 4 ml DPBS and 1 ml Cell reagent (Cellect Kit), centrifuged at 600 g, and re-suspended in 2 ml DPBS, the cells were applied onto Cellect column, and the eluted CD4+ cells were collected at $2 \times 10^6$/ml in 2% AM/medium containing human serum. 10 µl of 5 mM antibodies 1534, 1634, 1535, 1635, 3637 were added into the 96-well containing 100 µl of dendritic cells, and then mixed with 100 µl of CD4+ cells. The proliferation of activated. T cells was measured using alamarblue reagent. The result was converted into T cell Stimulation Index (SI). As shown in FIG. 13, the humanized anti-CD20 antibodies according to present invention exhibited lower T cell SI than that of Rituximab (FIG. 13). The result was consistent with that of in silicon in vitro immunogenicity assay, thus demonstrates that the immunogenicity of humanized anti-CD20 antibodies according to present invention was further reduced.

9. In Vitro Complement Dependent Cytotoxicity (CDC) Assay

Figure 14:
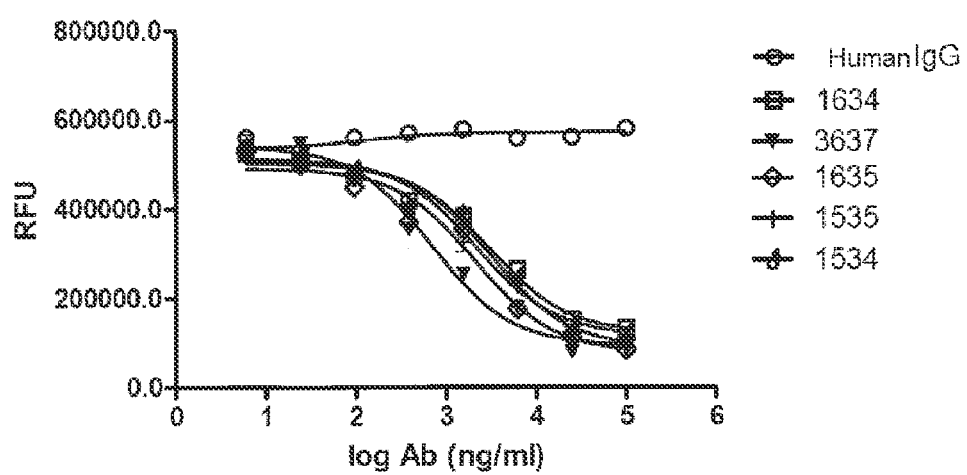
FIG. 14, Result of in vitro CDC effect of humanized anti-CD20 antibody on CD20+ Ramos lymphoma.

Ramos cells were harvested from RPMI suspension with a density of about $1 \times 10^6$/ml (containing 15% heat inactivated Gibco FBS), and cells were re-suspended in complete culture medium at a density of $4 \times 10^5$ cells/ml (RPMI+15% heat inactivated Gibco FBS), and then inoculated into a white flat-bottom 96-well plate at 25 µl/well. The culture medium was used to dilute the humanized anti-CD20 antibodies 1534, 1634, 1535, 1635, 3637 to ¼ appropriate concentration. Antibodies at 25 µl/well were added to cells in duplicate. Digitonin (Sigma, D5628) was prepared at 10 mg/ml in DMSO and diluted with culture medium to a concentration of 400 ug/ml. Digitonin at 25 µl/well was added to cells to provide maximum lysis. Media alone was added into wells to provide background lysis. Followed by the addition of 50 µl/well normal human serum from Biorclamation (containing human complement), the plate was incubated at room temperature for 10 minutes. The plate was then incubated at 37° C. for one hour. After incubation, 50 µl/well alamar blue was added and the plate was incubated overnight at 37° C. in 5% $CO_2$ incubator. Next day, the plate was placed on a shaker under room temperature for 15 min for cooling down. The fluorescence intensity was read using a 96-well fluorometer. The percent lysis was calculated as: % complement-dependent lysis= [(RFU test–REV background)/(RFU at maximum cell lysis–RFU background)]×100. Humanized anti-CD20 antibodies 1534, 1634, 1535, 1635, 3637 lyse approximately 50% of the Ramos target cells with an EC50 of 1.2 µg/ml-2.0 µg/ml. In contrast, no significant cell lysis was observed with control antibody (FIG. 14).

10. In Vitro Antibody-Dependent Cellular Cytotoxicity (ADCC) Assay

Blood obtained from normal volunteers was collected in heparinized syringes and mixed with equal volume of $Ca^{2+}$/$Mg^{2+}$ free HBSS (Life Technologies). Samples were subjected to lymphoprep gradient (Life Technologies) for separation and then centrifuged at 800 g for 30 min. PBMC located at the interface were harvested and washed in HEPES buffered saline and re-suspended in RPMI 1640 media (Life Technologies) (containing 1% heat-inactivated FBS (Hy-Clone Laboratories, Logan, UT), 2 nM L-glutamine, 10 mM HEPES and 50 mg/ml gentamicin). Ramos cells ($10^4$ cells/well) in 50 ml of assay buffer and varying concentrations of humanized anti-CD20 antibody 1534, 1634, 1535, 1635, 3637 (in 50 ml of assay buffer) were applied onto round-bottomed 96-well plate. The mixture was pre-inctibated for 30 min at 37° C. Then, 50 µL of the effector cells ($5\times10^5$) were dispensed into each well and incubated for 4 h at 37° C. A ratio of effector cells to target cells of 40:1 was used. The plate was centrifuged at 250 g for 10 min, and the supernatants were harvested. The activity of lactate dehydrogenase in the supernatants was determined using a Cytotoxic Detection kit (Boehringer Mannheim, Indianapolis, Ind.) according to the manufacturer's instruction.

Figure 15:
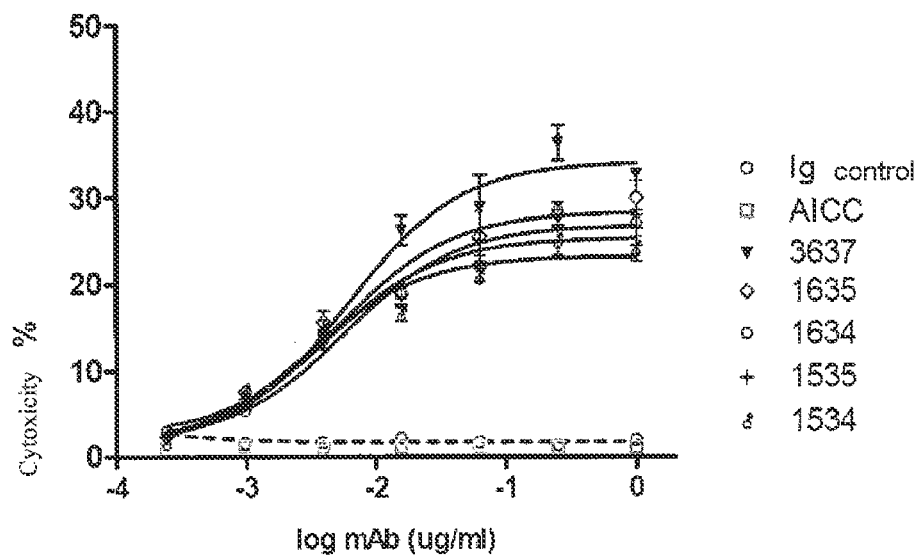
FIG. 15, Result of in vitro ADCC effect of humanized anti-CD20 antibody on CD20+ Ramos lymphoma.

The average absorbance of duplicates was used to calculate the percentage of cytotoxicity. During the 4-hour incubation, approximately 25-35% of CD20+ Ramos cells were lysed by humanized anti-CD20 antibodies 1534, 1634, 1535, 1635, 3637 (FIG. 15).

11. In Vivo Efficacy Studies in Animal

Figure 16:
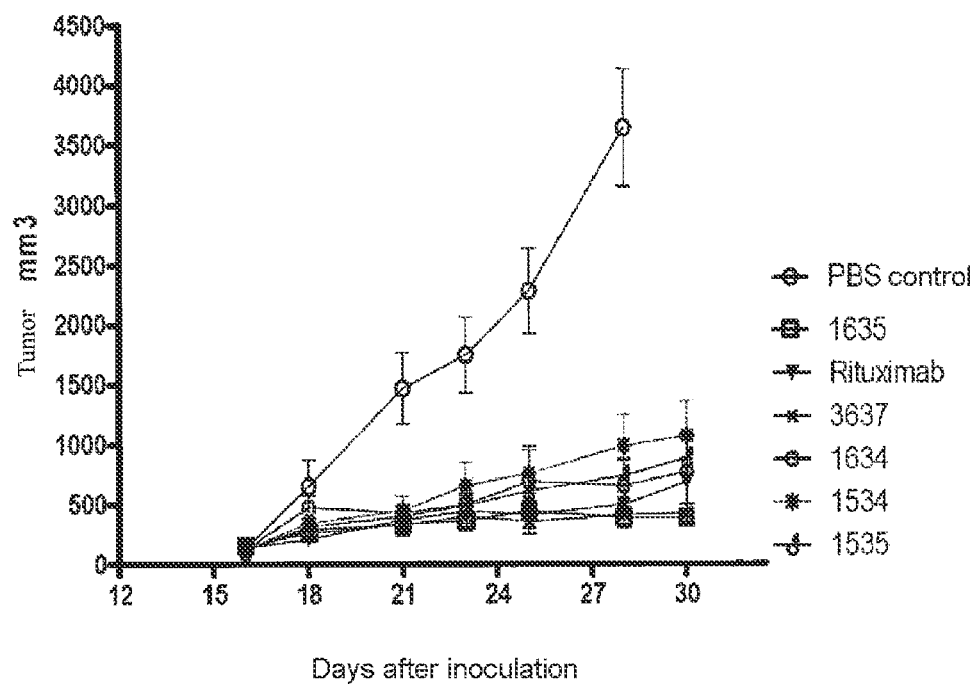
FIG. 16. Result of in vivo efficacy of humanized anti-CD20 antibody on CD20+ Ramos lymphoma.

Balb/c nude mice were inoculated subcutaneously with Ramos cells ($1\times10^7$ cells/0.1 ml/per mouse) on day 0. Tumor dimensions were determined by caliper measurements and tumor size was calculated using the formula: (length× width$^2$)/2. Tumor-bearing mice are randomized into 3 groups based on the tumor size, when the average tumor size reaches about 100 mm$^3$ (80-160 mm$^3$). Humanized anti-CD20 1534, 1634, 1535, 1635, 3637 (5 mg/kg), PBS (negative control) and Rituximab (5 mg/kg, positive control) were administrated intraperitoneally every Monday, Wednesday and Friday for a total of 2 weeks. Tumor sizes were measured on each Monday, Wednesday and Friday for a total of 2 weeks. As shown in FIG. 15, tumor sizes in control group rapidly increased up to >3000 mm$^3$ within 2 weeks. However, mice treated with either positive control rituximab or humanized anti-CD20 antibodies according to present invention significantly inhibited the tumor growth of mice, demonstrating similar or more potent antitumor activity of humanized anti-CD20 antibodies when compared with that of rituximab (FIG. 16).

---

What is claimed is:

1. A humanized anti-CD20 antibody, which comprises a heavy chain comprising a polypeptide according to one of SEQ ID NO: 15, SEQ ID NO: 16, or SEQ ID NO: 36; and a light chain comprising a polypeptide according to one of SEQ ID NO: 34, SEQ ID NO: 35, or SEQ ID NO: 37.

2. The antibodies as claimed in claim 1, which further comprises human IgG1 heavy chain constant region and human κ light chain constant region.

3. The antibody as claimed in claim 1, wherein the antibody is antibody 1534, 1634, 1535, 1635, 3637.

4. A composition for clinical treatment of B cell lymphoma, leukemia and various autoimmune diseases associated with B cell, comprising a formulation formed by the antibody as claimed in claim 1 and a pharmaceutically acceptable excipient.

5. An article of manufacture which comprises a container and a composition contained therein, wherein said composition is the composition as claimed in claim 4.

6. The antibodies as claimed in claim 1, wherein the antibody comprises one of:
   1) The sequence formed by the combination of SEQ ID NO: 15 and SEQ ID NO: 34;
   2) The sequence formed by the combination of SEQ ID NO: 16 and SEQ ID NO: 34;
   3) The sequence formed by the combination of SEQ ID NO: 15 and SEQ ID NO: 35;
   4) The sequence formed by the combination of SEQ ID NO: 16 and SEQ ID NO: 35; and
   5) The sequence formed by the combination of SEQ ID NO: 36 and SEQ ID NO: 37.

* * * * *

SEQUENCE LISTING

```
<160> NUMBER OF SEQ ID NOS: 40

<210> SEQ ID NO 1
<211> LENGTH: 30
<212> TYPE: PRT
<213> ORGANISM: Homo sapiens

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr
            20                  25                  30

<210> SEQ ID NO 2
<211> LENGTH: 30
<212> TYPE: PRT
<213> ORGANISM: Homo sapiens

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 3
<211> LENGTH: 30
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 4
<211> LENGTH: 14
<212> TYPE: PRT
<213> ORGANISM: Homo sapiens

<400> SEQUENCE: 4

Trp Val Lys Gln Thr Pro Gly Arg Gly Leu Glu Trp Ile Gly
```

<210> SEQ ID NO 5
<211> LENGTH: 14
<212> TYPE: PRT
<213> ORGANISM: Homo sapiens

<400> SEQUENCE: 5

Trp Val Arg Gln Pro Pro Gly Lys Gly Leu Glu Trp Ile Gly
1               5                   10

<210> SEQ ID NO 6
<211> LENGTH: 14
<212> TYPE: PRT
<213> ORGANISM: Homo sapiens

<400> SEQUENCE: 6

Trp Val Arg Gln Ala Pro Gly Lys Gly Leu Glu Trp Val Gly
1               5                   10

<210> SEQ ID NO 7
<211> LENGTH: 32
<212> TYPE: PRT
<213> ORGANISM: Homo sapiens

<400> SEQUENCE: 7

Lys Ala Thr Leu Thr Ala Asp Lys Ser Ser Thr Ala Tyr Met Gln
1               5                   10                  15

Leu Ser Ser Leu Thr Ser Glu Asp Ser Ala Val Tyr Tyr Cys Ala Arg
                20                  25                  30

<210> SEQ ID NO 8
<211> LENGTH: 32
<212> TYPE: PRT
<213> ORGANISM: Homo sapiens

<400> SEQUENCE: 8

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 9
<211> LENGTH: 32
<212> TYPE: PRT
<213> ORGANISM: Homo sapiens

<400> SEQUENCE: 9

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 10
<211> LENGTH: 11
<212> TYPE: PRT
<213> ORGANISM: Homo sapiens

<400> SEQUENCE: 10

Trp Gly Ala Gly Thr Thr Val Thr Val Ser Ala
1               5                   10

<210> SEQ ID NO 11

```
<210> SEQ ID NO 11
<211> LENGTH: 11
<212> TYPE: PRT
<213> ORGANISM: Homo sapiens

<400> SEQUENCE: 11

Trp Gly Gln Gly Thr Leu Val Thr Val Ser Ser
1               5                   10

<210> SEQ ID NO 12
<211> LENGTH: 11
<212> TYPE: PRT
<213> ORGANISM: Homo sapiens

<400> SEQUENCE: 12

Trp Gly Arg Gly Thr Leu Val Thr Val Ser Ser
1               5                   10

<210> SEQ ID NO 13
<211> LENGTH: 11
<212> TYPE: PRT
<213> ORGANISM: Homo sapiens

<400> SEQUENCE: 13

Trp Gly Gln Gly Thr Met Val Thr Val Ser Ser
1               5                   10

<210> SEQ ID NO 14
<211> LENGTH: 11
<212> TYPE: PRT
<213> ORGANISM: Homo sapiens

<400> SEQUENCE: 14

Trp Gly Gln Gly Thr Thr Val Thr Val Ser Ser
1               5                   10

<210> SEQ ID NO 15
<211> LENGTH: 121
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asn Met His Trp Val Arg Gln Pro Pro Gly Lys Gly Leu Glu Trp Ile
            35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
                100                 105                 110

Gln Gly Thr Thr Val Thr Val Ser Ser
            115                 120

<210> SEQ ID NO 16
<211> LENGTH: 121
<212> TYPE: PRT
<213> ORGANISM: Homo sapiens
```

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Lys Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Gln Gly Thr Thr Val Thr Val Ser Ser
        115                 120

<210> SEQ ID NO 17
<211> LENGTH: 23
<212> TYPE: PRT
<213> ORGANISM: Homo sapiens

<400> SEQUENCE: 17

Gln Ile Val Leu Ser Gln Ser Pro Ala Ile Leu Ser Ala Ser Pro Gly
1               5                   10                  15

Glu Lys Val Thr Met Thr Cys
            20

<210> SEQ ID NO 18
<211> LENGTH: 23
<212> TYPE: PRT
<213> ORGANISM: Homo sapiens

<400> SEQUENCE: 18

Asp Val Val Met Thr Gln Ser Pro Ala Phe Leu Ser Val Thr Pro Gly
1               5                   10                  15

Glu Lys Val Thr Ile Thr Cys
            20

<210> SEQ ID NO 19
<211> LENGTH: 23
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 20
<211> LENGTH: 15
<212> TYPE: PRT
<213> ORGANISM: Homo sapiens

<400> SEQUENCE: 20

Trp Phe Gln Gln Lys Pro Gly Ser Ser Pro Lys Pro Trp Ile Tyr
1               5                   10                  15

```
<210> SEQ ID NO 21
<211> LENGTH: 15
<212> TYPE: PRT
<213> ORGANISM: Homo sapiens

<400> SEQUENCE: 21

Trp Phe Gln Gln Lys Pro Gly Lys Ala Pro Lys Ser Leu Ile Tyr
1               5                   10                  15

<210> SEQ ID NO 22
<211> LENGTH: 32
<212> TYPE: PRT
<213> ORGANISM: Homo sapiens

<400> SEQUENCE: 22

Gly Val Pro Val Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Tyr Cys
            20                  25                  30

<210> SEQ ID NO 23
<211> LENGTH: 32
<212> TYPE: PRT
<213> ORGANISM: Homo sapiens

<400> SEQUENCE: 23

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 24
<211> LENGTH: 32
<212> TYPE: PRT
<213> ORGANISM: Homo sapiens

<400> SEQUENCE: 24

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 25
<211> LENGTH: 32
<212> TYPE: PRT
<213> ORGANISM: Homo sapiens

<400> SEQUENCE: 25

Gly Ile Pro Ala Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 26
<211> LENGTH: 32
<212> TYPE: PRT
<213> ORGANISM: Homo sapiens

<400> SEQUENCE: 26

Gly Ile Pro Ala Arg Phe Ser Gly Ser Gly Ser Gly Thr Asp Phe Thr
1               5                   10                  15
```

Leu Thr Ile Ser Arg Leu Gln Ser Glu Asp Phe Ala Val Tyr Tyr Cys
          20                  25                  30

<210> SEQ ID NO 27
<211> LENGTH: 32
<212> TYPE: PRT
<213> ORGANISM: Homo sapiens

<400> SEQUENCE: 27

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
          20                  25                  30

<210> SEQ ID NO 28
<211> LENGTH: 11
<212> TYPE: PRT
<213> ORGANISM: Homo sapiens

<400> SEQUENCE: 28

Trp Gly Ala Gly Thr Thr Val Thr Val Ser Ala
1               5                   10

<210> SEQ ID NO 29
<211> LENGTH: 10
<212> TYPE: PRT
<213> ORGANISM: Homo sapiens

<400> SEQUENCE: 29

Phe Gly Gln Gly Thr Lys Val Glu Ile Lys
1               5                   10

<210> SEQ ID NO 30
<211> LENGTH: 10
<212> TYPE: PRT
<213> ORGANISM: Homo sapiens

<400> SEQUENCE: 30

Phe Gly Gln Gly Thr Lys Leu Glu Ile Lys
1               5                   10

<210> SEQ ID NO 31
<211> LENGTH: 10
<212> TYPE: PRT
<213> ORGANISM: Homo sapiens

<400> SEQUENCE: 31

Phe Gly Pro Gly Thr Lys Val Asp Ile Lys
1               5                   10

<210> SEQ ID NO 32
<211> LENGTH: 10
<212> TYPE: PRT
<213> ORGANISM: Homo sapiens

<400> SEQUENCE: 32

Phe Gly Gly Gly Thr Lys Val Glu Ile Lys
1               5                   10

<210> SEQ ID NO 33
<211> LENGTH: 10
<212> TYPE: PRT
<213> ORGANISM: Homo sapiens

<400> SEQUENCE: 33

Phe Gly Gln Gly Thr Arg Leu Glu Ile Lys
1               5                   10

<210> SEQ ID NO 34
<211> LENGTH: 106
<212> TYPE: PRT
<213> ORGANISM: Homo sapiens

<400> SEQUENCE: 34

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Ile
            20                  25                  30

His Trp Phe Gln Gln Lys Pro Gly Lys Ala Pro Lys Ser Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Val Glu Ile Lys
            100                 105

<210> SEQ ID NO 35
<211> LENGTH: 106
<212> TYPE: PRT
<213> ORGANISM: Homo sapiens

<400> SEQUENCE: 35

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Ile
            20                  25                  30

His Trp Phe Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Val Glu Ile Lys
            100                 105

<210> SEQ ID NO 36
<211> LENGTH: 121
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Lys Gly Leu Glu Trp Ile
        35                  40                  45

```
Gly Ala Ile Tyr Pro Gly Asn Ser Asp Thr Asn Tyr Asn Gln Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Thr Tyr Tyr Gly Gly Asp Trp Asn Phe Glu Val Trp Gly
            100                 105                 110

Gln Gly Thr Thr Val Thr Val Ser Ser
            115                 120

<210> SEQ ID NO 37
<211> LENGTH: 106
<212> TYPE: PRT
<213> ORGANISM: Homo sapiens

<400> SEQUENCE: 37

Asp Val Val Met Thr Gln Ser Pro Ala Phe Leu Ser Val Thr Pro Gly
 1               5                  10                  15

Glu Lys Val Thr Ile Thr Cys Arg Ala Ser Ser Ser Val Ser Tyr Ile
                20                  25                  30

His Trp Phe Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
         50                 55                  60

Gly Ser Gly Thr Asp Phe Thr Leu Thr Ile Asn Ser Leu Glu Ala Glu
 65                 70                  75                  80

Asp Ala Ala Thr Tyr Tyr Cys Gln Gln Trp Thr Ser Lys Pro Pro Thr
                85                  90                  95

Phe Gly Gly Gly Thr Lys Val Glu Ile Lys
            100                 105

<210> SEQ ID NO 38
<211> LENGTH: 15
<212> TYPE: PRT
<213> ORGANISM: Homo sapiens

<400> SEQUENCE: 38

Trp Tyr Gln Gln His Pro Gly Thr Val Pro Lys Pro Met Ile Tyr
 1               5                  10                  15

<210> SEQ ID NO 39
<211> LENGTH: 15
<212> TYPE: PRT
<213> ORGANISM: Homo sapiens

<400> SEQUENCE: 39

Trp Phe Gln Gln Lys Pro Gly Gln Ala Pro Arg Ala Leu Ile Tyr
 1               5                  10                  15

<210> SEQ ID NO 40
<211> LENGTH: 15
<212> TYPE: PRT
<213> ORGANISM: Homo sapiens

<400> SEQUENCE: 40

Trp Phe Gln Gln Lys Pro Gly Gln Ala Pro Arg Thr Leu Ile Tyr
 1               5                  10                  15
```